(12) United States Patent
Sawyer

(10) Patent No.: US 12,723,704 B2
(45) Date of Patent: Sep. 1, 2026

(54) LIGHT THERAPY DEVICE STAND

(71) Applicant: Mark Sawyer, Lake Mary, FL (US)

(72) Inventor: Mark Sawyer, Lake Mary, FL (US)

(73) Assignee: Platinum IP LLC, Wilmington, DE (US)

( * ) Notice: Subject to any disclaimer, the term of this patent is extended or adjusted under 35 U.S.C. 154(b) by 196 days.

(21) Appl. No.: 18/798,360

(22) Filed: Aug. 8, 2024

(65) Prior Publication Data

US 2025/0195910 A1 Jun. 19, 2025

Related U.S. Application Data

(63) Continuation of application No. 18/643,452, filed on Apr. 23, 2024.

(60) Provisional application No. 63/612,237, filed on Dec. 19, 2023, provisional application No. 63/612,108, filed on Dec. 19, 2023.

(51) Int. Cl.

| | |
|---|---|
| ***F16M 11/00*** | (2006.01) |
| ***F16M 11/26*** | (2006.01) |
| *A61N 5/06* | (2006.01) |
| *F16M 11/42* | (2006.01) |

(52) U.S. Cl.
CPC ..... *F16M 11/26* (2013.01); *A61N 2005/0652* (2013.01); *F16M 11/42* (2013.01)

(58) Field of Classification Search
None
See application file for complete search history.

(56) References Cited

U.S. PATENT DOCUMENTS 3,848,870 A 11/1974 Craig
4,715,701 A * 12/1987 Urban .................. B60R 1/0605 248/467

(Continued)

FOREIGN PATENT DOCUMENTS

| | | |
|---|---|---|
| CA | 2034511 A1 | 7/1992 |
| CN | 106195587 A | 12/2016 |

(Continued)

OTHER PUBLICATIONS

International Search Report and Written Opinion; PCT/US2024/059355; mailed Feb. 18, 2025.

(Continued)

*Primary Examiner* — Steven M Marsh
(74) *Attorney, Agent, or Firm* — Jason T. Daniel, Esq.; Daniel Law Offices, P.A.

(57) ABSTRACT

A light therapy device stand includes a base, a telescoping extension arm, a receptacle connected to the extension arm, an elongated support bar, a plurality of sliding connectors, a plurality of connection rails, and a plurality of extension rails. Individual light therapy devices can be secured onto the support bar via the sliding connectors. Standard sized light therapy devices can be secured onto the support bar in a stacked configuration via the connection rails, and non-standard sized light therapy devices can be secured onto the support bar in a stacked configuration via the extension rails. The support bar rotates 90 degrees relative to the extension arm to transition each connected light therapy device between a vertical orientation and a horizontal orientation.

10 Claims, 19 Drawing Sheets

(56) References Cited

U.S. PATENT DOCUMENTS 4,730,386 A * 3/1988 Fieberg .................. H01R 43/22 81/176.1
4,866,284 A 9/1989 Frankena et al.
5,058,848 A * 10/1991 Ferraro ................ A47B 23/007 248/445
5,293,835 A * 3/1994 Shagoury ........... A01K 39/0113 119/57.9
5,616,140 A 4/1997 Prescott
5,733,032 A 3/1998 Bolta et al.
6,430,761 B1 8/2002 Brandorff et al.
7,246,463 B1 * 7/2007 Arnot ................. A47G 33/1246 47/42
7,514,619 B1 * 4/2009 Bruce .................... A47B 81/00 248/463
8,070,114 B2 12/2011 Chen
8,074,815 B2 12/2011 Gerstner
8,469,323 B1 6/2013 Deros et al.
8,613,454 B2 12/2013 Foley
D774,322 S 12/2016 Schmauch et al.
10,478,635 B1 11/2019 Nelson et al.
10,485,983 B1 11/2019 Boone, III et al.
10,639,495 B1 5/2020 Nelson et al.
10,828,505 B2 11/2020 Nelson et al.
11,033,752 B2 6/2021 Strahan et al.
11,253,719 B2 2/2022 Strahan et al.
11,524,172 B2 12/2022 Strahan et al.
11,535,288 B2 12/2022 Leblanc
12,569,059 B2 * 3/2026 Zebarjad .................. A47B 9/10
2004/0111132 A1 6/2004 Shenderova et al.
2004/0181268 A1 * 9/2004 Anderer ............... A61N 5/0619 607/90
2005/0167552 A1 * 8/2005 Tourtellotte ........ E04H 12/2238 248/158
2008/0039910 A1 2/2008 Chen
2014/0128941 A1 5/2014 Williams et al.
2015/0313181 A1 * 11/2015 Burroughs ............ F21V 21/145 362/253
2016/0016001 A1 1/2016 Loupis et al.
2016/0256706 A1 9/2016 Harrison
2019/0137083 A1 5/2019 Liu et al.
2019/0216927 A1 7/2019 Lundahl et al.
2020/0316398 A1 10/2020 Salinas et al.
2021/0236838 A1 * 8/2021 Pfiffner .................... A61N 5/06
2021/0393973 A1 12/2021 Ruzicka
2022/0016435 A1 1/2022 Pfiffner
2022/0280807 A1 9/2022 van de Ven et al.
2022/0339460 A1 10/2022 Forhan
2023/0132952 A1 5/2023 Youngblood et al.
2023/0414962 A1 12/2023 Sawyer
2025/0248493 A1 * 8/2025 Jones ..................... A45B 23/00

FOREIGN PATENT DOCUMENTS

CN 207112276 3/2018
CN 109289127 A 2/2019
CN 210624081 U 5/2020
CN 111678062 A 9/2020
CN 211902293 U 11/2020
CN 215258771 12/2021
CN 217235199 8/2022
CN 218762452 U 3/2023
CN 219878954 U 10/2023

OTHER PUBLICATIONS

International Search Report and Written Opinion; PCT/US2024/042905; mailed Nov. 1, 2024 (9 pages).

International Search Report and Written Opinion; PCT/US2024/036399; Oct. 10, 2024 (11 pages).

International Search Report and Written Opinion for International Patent Application PCT/US2024/052622, mailed Jan. 2, 2025 (8 pages).

* cited by examiner

LIGHT THERAPY DEVICE STAND

CROSS-REFERENCE TO RELATED APPLICATIONS

This application claims the benefit of U.S. Application Ser. No. 63/612,108 filed on Dec. 19, 2023, and U.S. patent application Ser. No. 18/643,452 filed on Apr. 23, 2024, the contents of each of which are incorporated herein by reference.

TECHNICAL FIELD

The present invention relates generally to the field of light therapy devices, and more particularly to a stand for positioning one or more light therapy devices in a specified orientation.

BACKGROUND

The statements in this section merely provide background information related to the present disclosure and may not constitute prior art.

Scientific research has shown that exposing human skin to certain types of light can have a meaningful effect on the person's overall health. Depending on the intensity and spectrum/wavelength of the light, these effects can include reducing stress, eliminating headaches, promoting hair growth, increasing collagen production, reducing the appearance of acne, and even fat reduction.

Many commercially available light therapy devices are manufactured to include an industry standard height/length of about 19 inches and a width of about 8-10 inches so as to be suitable for providing light therapy to a single area of a user's body such as the head, chest, or back, for example. In this regard, it is important that a user be able to accurately position the device to ensure the desired portion of their body receives the treatment.

Most commercially available light therapy devices are provided with a mounting kit having a pair of posts that are screwed into the top surface of the device which engage a pair of elongated cords and a pulley system to allow the device to be suspended from a door or wall via a hook. However, if/when users seek to link multiple devices together side by side, they must use two separate mounting systems. When the user seeks to link multiple devices together vertically, they must connect the panels to each other using the above noted posts and keyhole openings in the bottom of each device.

Although there are known types of light therapy stands which can individually engage a light therapy device, such stands are cumbersome to use, and do not provide the ability for a user to easily maneuver one or more light therapy devices in unison to direct the light emissions in a plurality of different orientations. Additionally, such devices do not allow a user to rotate multiple light therapy devices so as to be positioned in either a horizontal or vertical manner for use when standing or lying down. Moreover, such devices require the user to physically lift the device when changing the orientation, which is difficult due to the weight of the devices and may not be possible for individuals suffering from or recovering from certain injuries.

The present invention, directed to a light therapy device stand differs from the conventional art in several aspects. The manner by which will become more apparent in the description which follows, particularly when read in conjunction with the accompanying drawings.

SUMMARY OF THE INVENTION

The present invention is directed to a light therapy device stand. One embodiment of the present invention can include a base having a pair of horizontal L-shaped base members, and a vertically oriented extension arm. The extension arm can include a fixed arm section having a bottom end that is connected to the base members, a hollow interior space, and an upper end having an opening into which a sliding arm section is positioned. A receptacle can be positioned along the top end of the sliding arm section and can receive an elongated support bar onto which one or more light therapy devices can be connected.

In one embodiment, a plurality of sliding connectors are located along the support bar. Each of the connectors can function to engage and position a single light therapy device onto the support bar. In one embodiment, two light therapy devices can be positioned side by side along the length of the support bar.

In one embodiment, a plurality of connection rails can engage the sliding connectors and can engage and position two standard sized light therapy devices onto the support bar in a stacked orientation. In one embodiment, four standard sized light therapy devices can be positioned in a 2×2 stacked and side by side orientation along the length of the support bar.

In one embodiment, a plurality of extension rails can engage the connection rails and can secure and position two non-standard sized light therapy devices onto the support bar in a stacked orientation. In one embodiment, four non-standard sized light therapy devices can be positioned in a 2×2 stacked and side by side orientation along the length of the support bar.

In one embodiment, the elongated support bar can rotate 90 degrees relative to the extension arm to transition any number of attached light therapy devices between a vertical orientation and a horizontal orientation.

This summary is provided merely to introduce certain concepts and not to identify key or essential features of the claimed subject matter.

BRIEF DESCRIPTION OF THE DRAWINGS

Presently preferred embodiments are shown in the drawings. It should be appreciated, however, that the invention is not limited to the precise arrangements and instrumentalities shown.

FIG. 7C is yet another side view of the light therapy device stand in operation, in accordance with one embodiment of the invention.

DETAILED DESCRIPTION OF THE INVENTION

Figure 1:
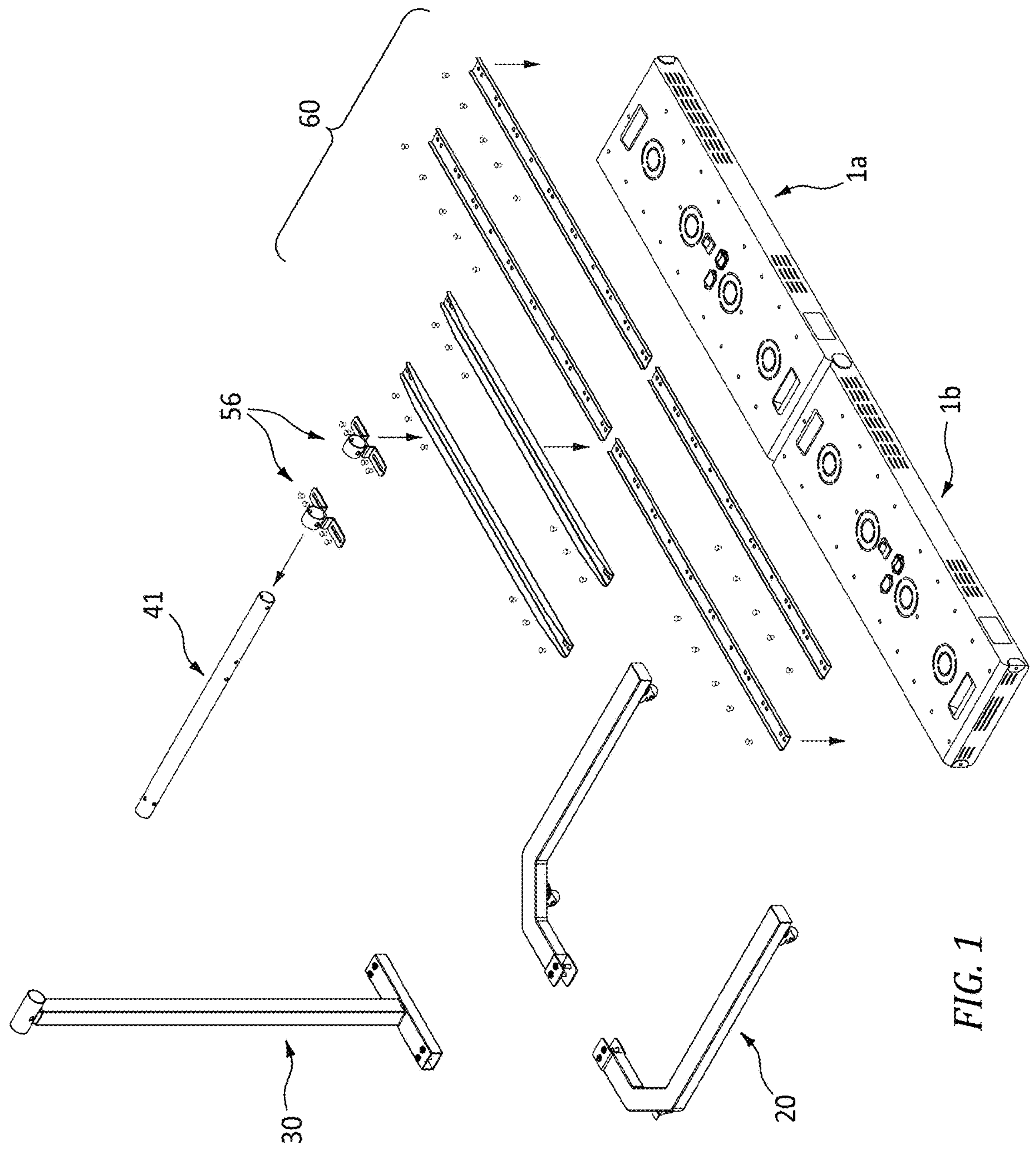
FIG. 1 is an exploded parts view of a light therapy device stand that is useful for understanding the inventive concepts disclosed herein.
Figure 2:
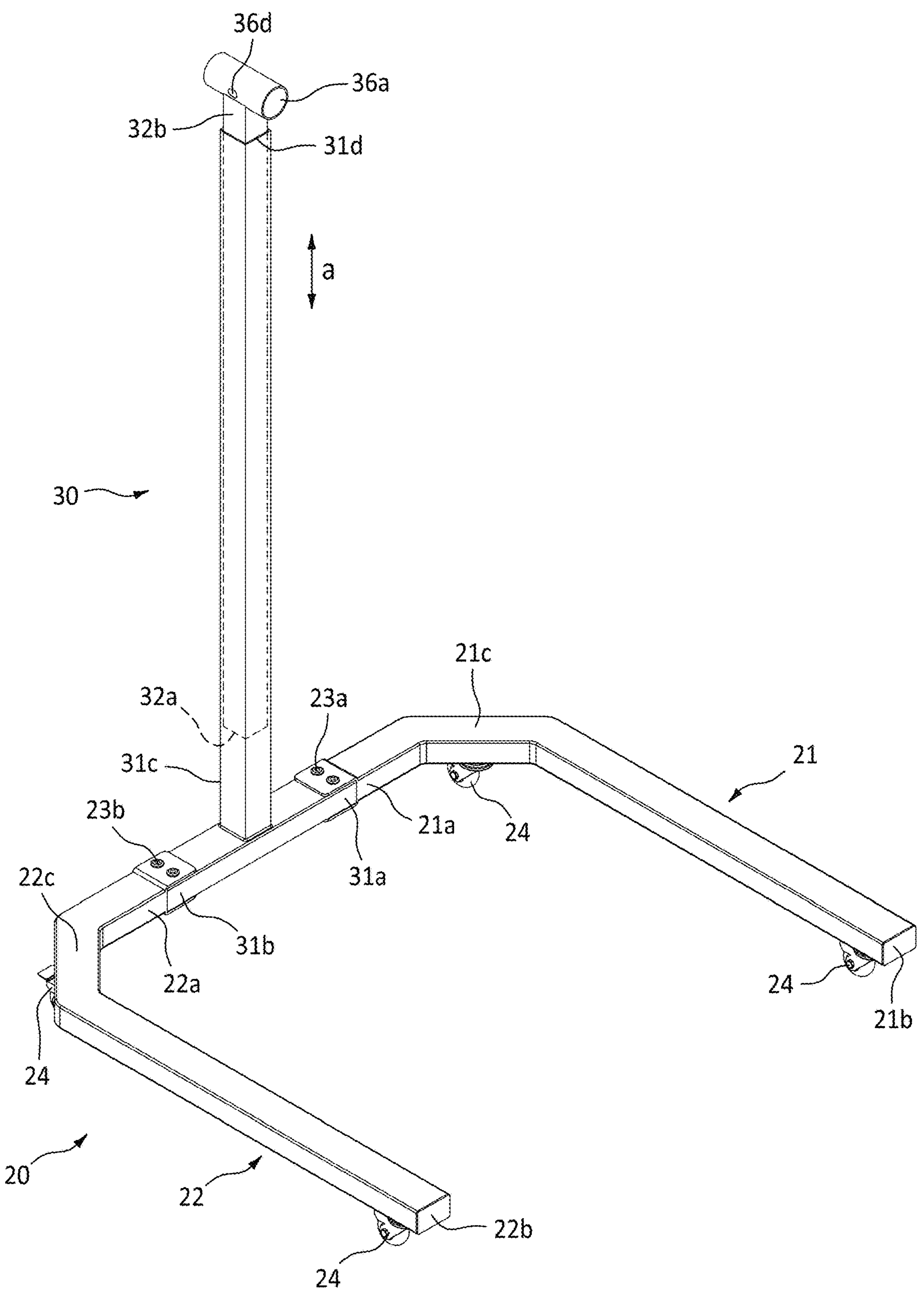
FIG. 2 is a perspective view of the base and extension arm of the light therapy device stand in the retracted position, in accordance with one embodiment of the invention.
Figure 3:
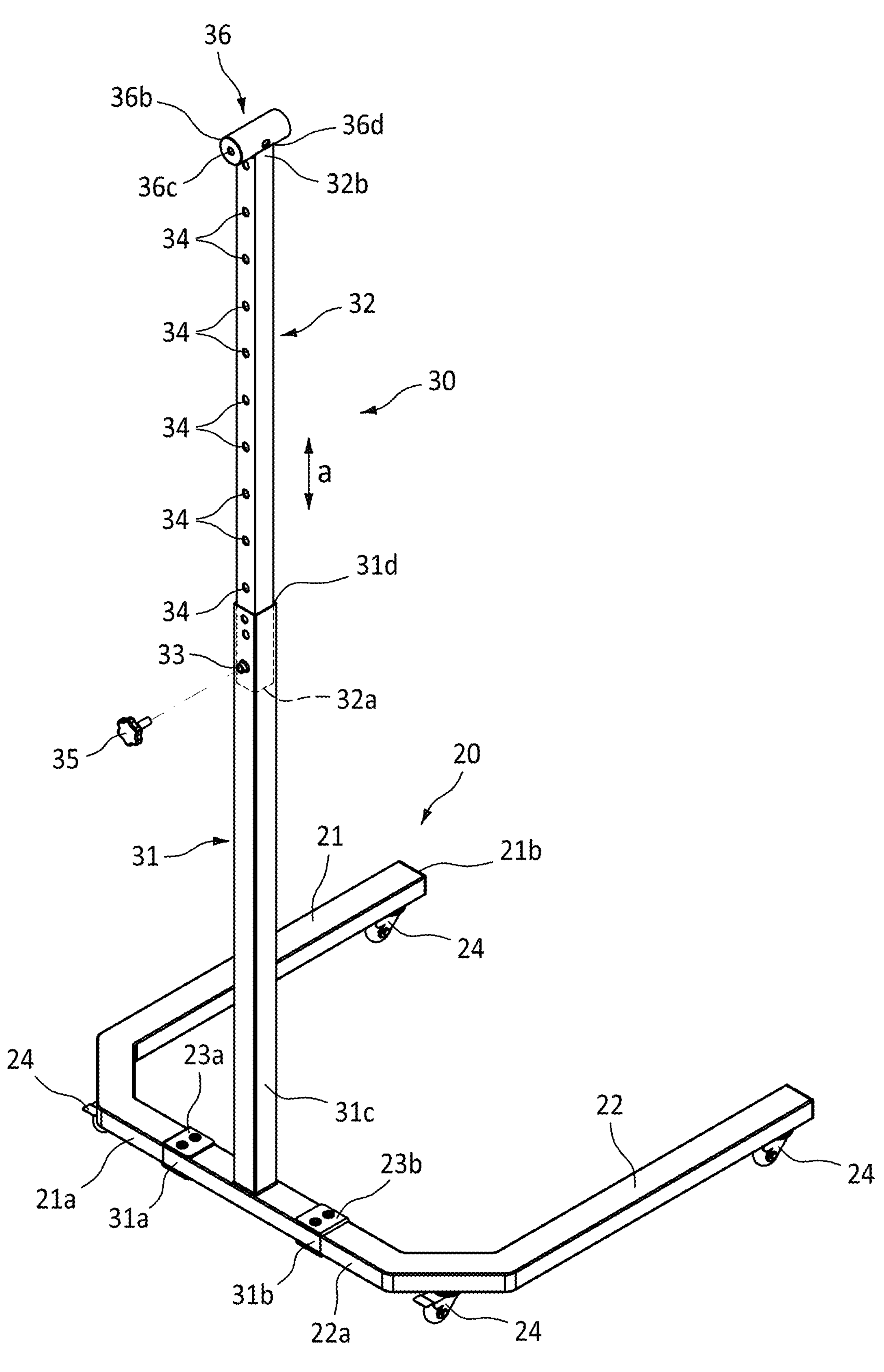
FIG. 3 is a perspective view of the base and extension arm of the light therapy device stand in the extended position, in accordance with one embodiment of the invention.

While the specification concludes with claims defining the features of the invention that are regarded as novel, it is believed that the invention will be better understood from a consideration of the description in conjunction with the drawings. As required, detailed embodiments of the present invention are disclosed herein; however, it is to be understood that the disclosed embodiments are merely exemplary of the invention which can be embodied in various forms. Therefore, specific structural and functional details disclosed herein are not to be interpreted as limiting, but merely as a basis for the claims and as a representative basis for teaching one skilled in the art to variously employ the inventive arrangements in virtually any appropriately detailed structure. Further, the terms and phrases used herein are not intended to be limiting but rather to provide an understandable description of the invention.

Definitions

As described herein, a “unit” and “section” mean a series of identified physical components which are linked together and/or function together to perform a specified function.

As described throughout this document, the term “about” “approximately” “substantially” and “generally” shall be used interchangeably to describe a feature, shape, or measurement of a component within a tolerance such as, for example, manufacturing tolerances, measurement tolerances or the like.

As described herein, the term “removably secured,” and derivatives thereof shall be used to describe a situation wherein two or more objects are joined together in a non-permanent manner so as to allow the same objects to be repeatedly joined and separated.

As described throughout this document, the term “complementary shape,” and “complementary dimension,” shall be used to describe a shape and size of a component that is identical to, or substantially identical to the shape and size of another identified component within a tolerance such as, for example, manufacturing tolerances, measurement tolerances or the like.

As described herein, the term “slidingly engage”, “telescopically connected” and derivatives thereof shall be used interchangeably to describe a situation wherein two or more identified objects are connected linearly such that one identified part slides into and out from the other identified part so as to selectively lengthen or shorten the total linear length of the assembly.

FIGS. 1-7D illustrate one embodiment of a light therapy device stand 10 that are useful for understanding the inventive concepts disclosed herein. In each of the drawings, identical reference numerals are used for like elements of the invention or elements of like function. For the sake of clarity, only those reference numerals are shown in the individual figures which are necessary for the description of the respective figure. For purposes of this description, the terms “upper,” “bottom,” “right,” “left,” “front,” “vertical,” “horizontal,” and derivatives thereof shall relate to the invention as oriented in FIG. 1.

As described herein, the inventive stand 10 can function to engage and position one or more light therapy devices such as those described in copending U.S. patent application Ser. No. 18/643,442 to Sawyer, the contents of which are incorporated herein by reference. However, other types of light therapy devices may also be used.

As shown in the drawings, one embodiment of the light therapy device stand 10 for engaging and positioning one or more light therapy devices 1 can include, essentially, a base 20, an extension arm 30, a support bar 41, and a panel attachment assembly 60.

The base 20 can form the bottom end of the stand 10 and can function to provide a stable platform from which the extension arm and panel connection assembly can extend. In one embodiment, the base can include two generally L-shaped members 21 and 22, each having a first end 21*a* and 22*a*, a second end 21*b* and 22*b*, and a curved section 21*c* and 22*c*, respectively.

In one embodiment, mounting brackets 23*a* and 23*b* can be positioned along the first ends 21*a* and 22*a* for securing the base members onto the extension arm 30, and a plurality of single-direction or omnidirectional casters 24 can be provided to allow the assembled stand to be easily moved from one location to another.

As described herein, the base 20 may be formed from materials that are, for example, relatively strong and stiff for their weight. Several nonlimiting examples include but are not limited to various metals or metal alloys (e.g., aluminum, steel, titanium, or alloys thereof), plastic/polymers (e.g., high-density polyethylene (HDPE), rigid polyvinyl chloride (PVC), malleable polyethylene terephthalate (PET)), and/or various composite materials. Although described above with regard to a U-shaped base member shape, this is for illustrative purposes only, as any number of other configurations are also contemplated.

The extension arm 30 can include a generally inverted T-shaped fixed arm section 31 having a first bottom end 31*a*, a second bottom end 31*b*, an elongated hollow middle portion 31*c* and an open top end 31*d*. The first and second ends 31*a* and 31*b* can be connected to the first ends 21*a* and 22*a* of the first and second base members via brackets 23*a* and 23*b*, respectively, so as to orient the fixed arm section vertically when the base is positioned horizontally.

In one embodiment, the extension arm 30 also includes a sliding arm section 32 having a bottom end 32*a* and a top end 32*b*. As shown by arrow a, the sliding arm section can be positioned through the open top end 31*d* so as to extend from and retract into the hollow middle portion 31*c* of the fixed arm section. In this regard, the sliding arm section can be positioned anywhere between the fully retracted position shown at FIG. 2, and the fully extended position shown at FIG. 3.

In one embodiment, a positioning opening 33 is located along the fixed bar section 31, and a plurality of alignment openings 34 are located along the length of the sliding bar section 32. The height of the sliding bar section can be set via a locking pin 35 or other such device that positioned through the positioning opening 33 and one of the alignment openings 34. Of course, any number of other mechanisms such as a tensioning ring, for example can be provided to secure the sliding bar section at a user defined height.

In one embodiment, a receptacle 36 is positioned along the top end of the sliding arm section 32*b*. As shown the receptacle can include a generally hollow and cylindrical-shaped member having an open first end 36*a*, a closed back end 36*b*, a back opening 36*c* and a side opening 36*d* along the sidewall. The hollow interior space formed by the receptacle will include a shape and size that is complementary to the shape and size of one end of the below described support bar 41 so as to removably and rotatably engage bar to orient one or more light therapy devices in any number of user-desired manners.

In either instance, each of the fixed arm section and the sliding arm section may also be formed from materials that are, for example, relatively strong and stiff for their weight. Several nonlimiting examples include but are not limited to various metals or metal alloys, various plastics/polymers, and/or various composite materials.

Figure 4:
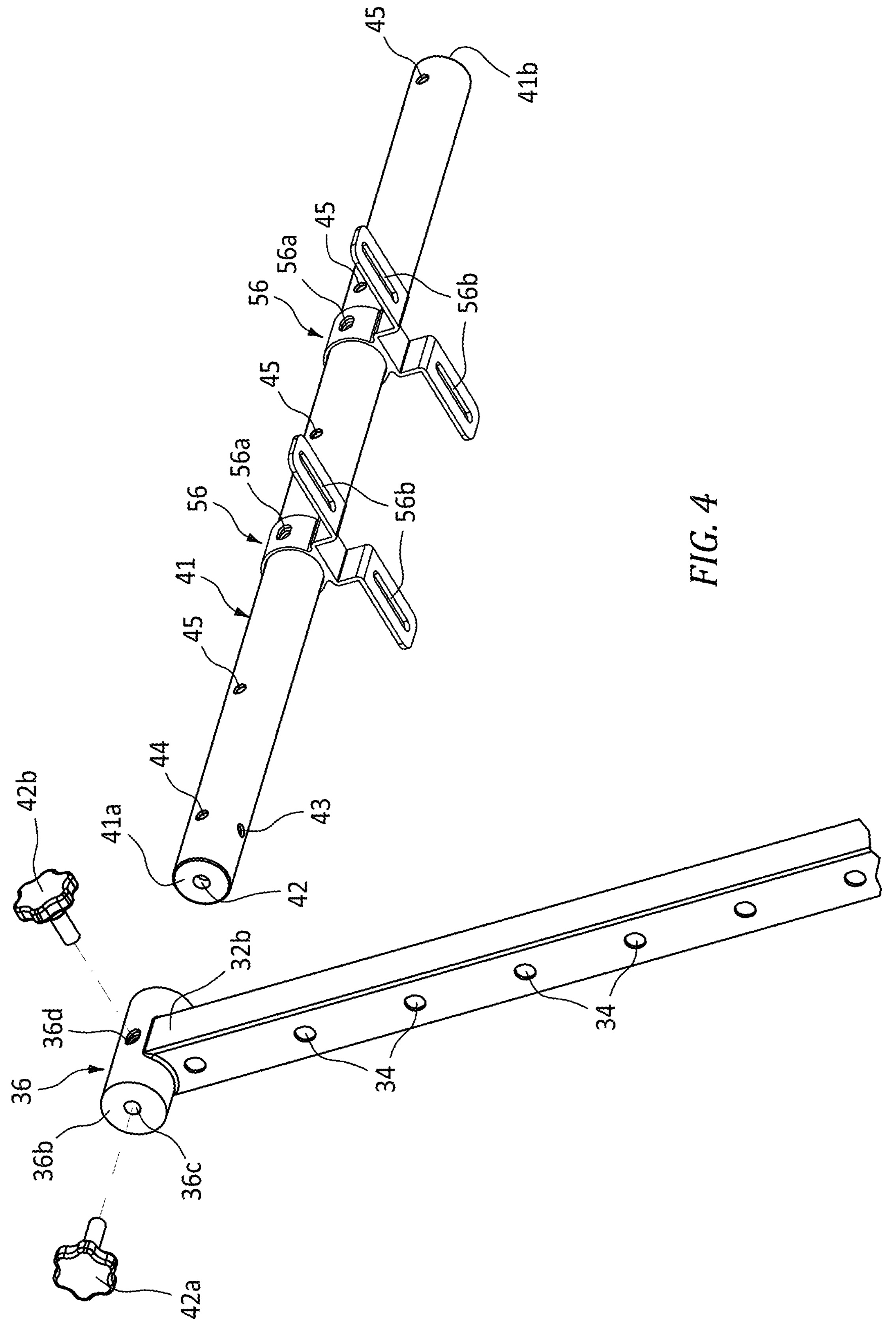
FIG. 4 is a cutout view of the support bar and extension arm of the light therapy device stand, in accordance with one embodiment of the invention.

FIG. 4 illustrates one embodiment of the horizontal support bar 41 having a first end 41*a*, a second end 41*b*, a lateral threaded opening 42, a vertical-positioning threaded opening 43 a horizontal-positioning threaded opening 44 and a plurality of sliding panel threaded openings 45 that are aligned serially with each other and the horizontal-positioning threaded opening 44.

In the preferred embodiment, the bar 41 can be constructed from a solid rigid material such as aluminum or steel round bar, for example, however other shapes and construction materials are also contemplated.

In one embodiment, a plurality of sliding connectors 56 can be connected to the bar. Each of the sliding connectors can include a generally horseshoe-shaped member having a cylindrical-shaped center section with a center opening 56*a*, and two serially aligned connection arms with slotted openings 56*b* extending outward therefrom along an identical plane. As described herein, the cylindrical central section of each connector 56 can include a shape and size that is complementary to the cross-sectional shape and size of the bar 41 and can function to slide along the length thereof.

As shown best at FIGS. 5A-5D, each of the sliding connectors 56 can form part of the can function to secure one or more light therapy devices 1 onto the support bar so as to be oriented in a user-defined manner by the stand. In this regard, the center opening of each sliding connector can be aligned with one of the plurality of threaded apertures 45 along the length of the support bar 41 and can function to receive mounting hardware such as a bolt 3, for example, that passes through the opening 56*a* and engages the aperture 45 to secure the connector to the bar.

In one embodiment, each of the sliding connectors 56 can also include elongated slotted openings 56*b* along the connection arms. Each of the slotted openings 56*b* are spaced at locations complementary to the locations of the mounting apertures 2 located along the back surface of a light therapy device 1. In this regard, additional mounting hardware such as a bolt 3, for example, can pass through the openings 56*b* to engage the mounting apertures 2 on the light therapy device 1 to secure the device onto the sliding connector.

As noted above, the support bar 41 is removably and rotatably secured onto the extension arm 30 via the receptacle 36. As such, the lateral threaded opening 42 is positioned along the end of the bar 41*a* so as to be aligned with the back opening 36*c* when the bar is positioned within the receptacle 36. When so positioned, a first thumbscrew 42*a* or other such hardware can pass through the opening 36*c* to engage the lateral threaded opening 42 in order to secure the bar onto the extension arm and to prevent lateral separation of the same.

The vertical-positioning threaded opening 43 is positioned at a 90° angle relative to the horizontal-positioning threaded opening 44, and both openings include a separation distance from the first end 41*a* that is complementary to the separation distance at which the side opening 36*d* is positioned relative to the back opening 36*c* on the receptacle 36. Both threaded openings can be selectively engaged by a second thumbscrew 42*b* or other such hardware that can pass through the side opening of the receptacle.

Figure 5A:
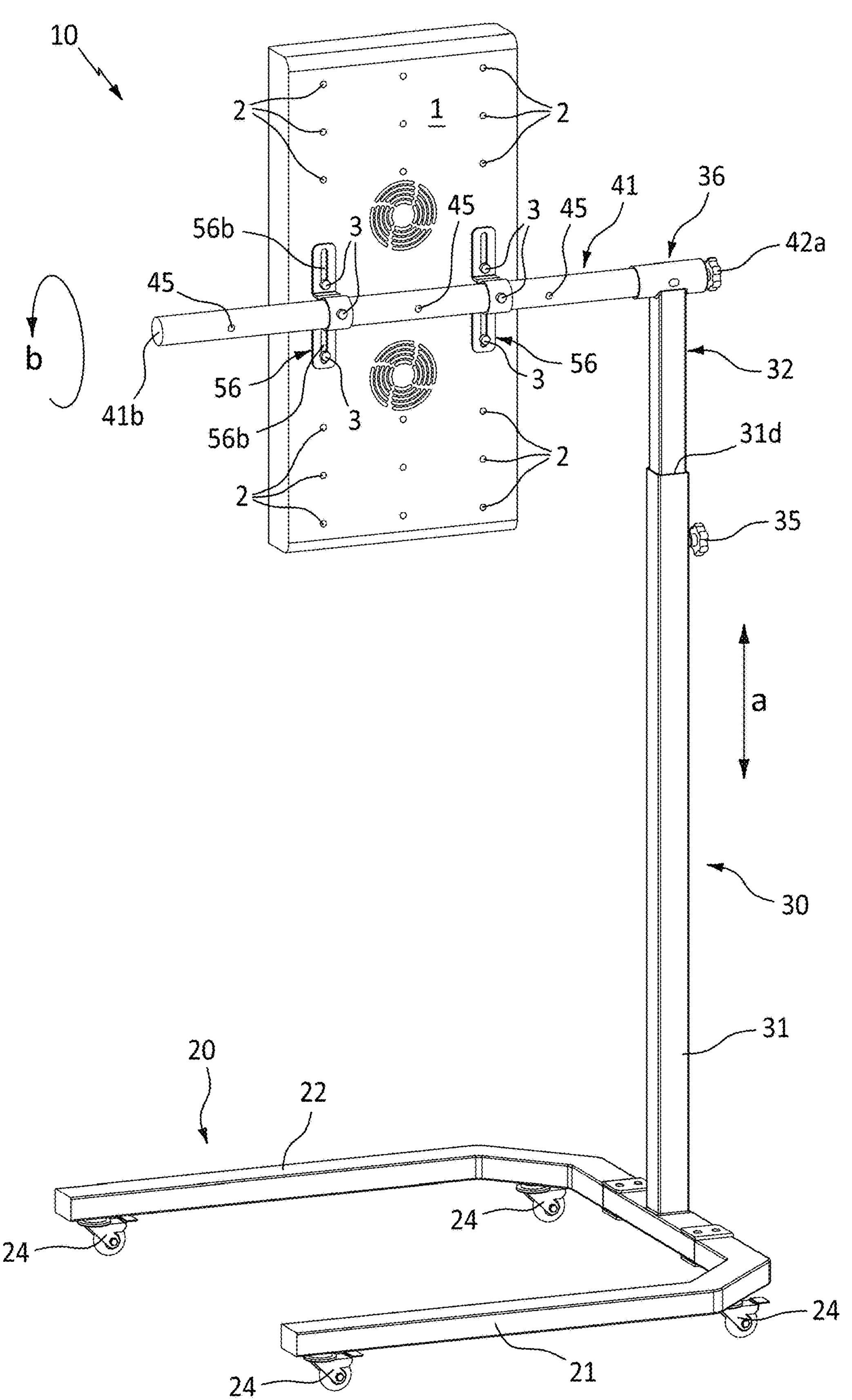
FIG. 5A is a cutout view of the panel attachment assembly of the light therapy device stand, in accordance with one embodiment of the invention.
Figure 5B:
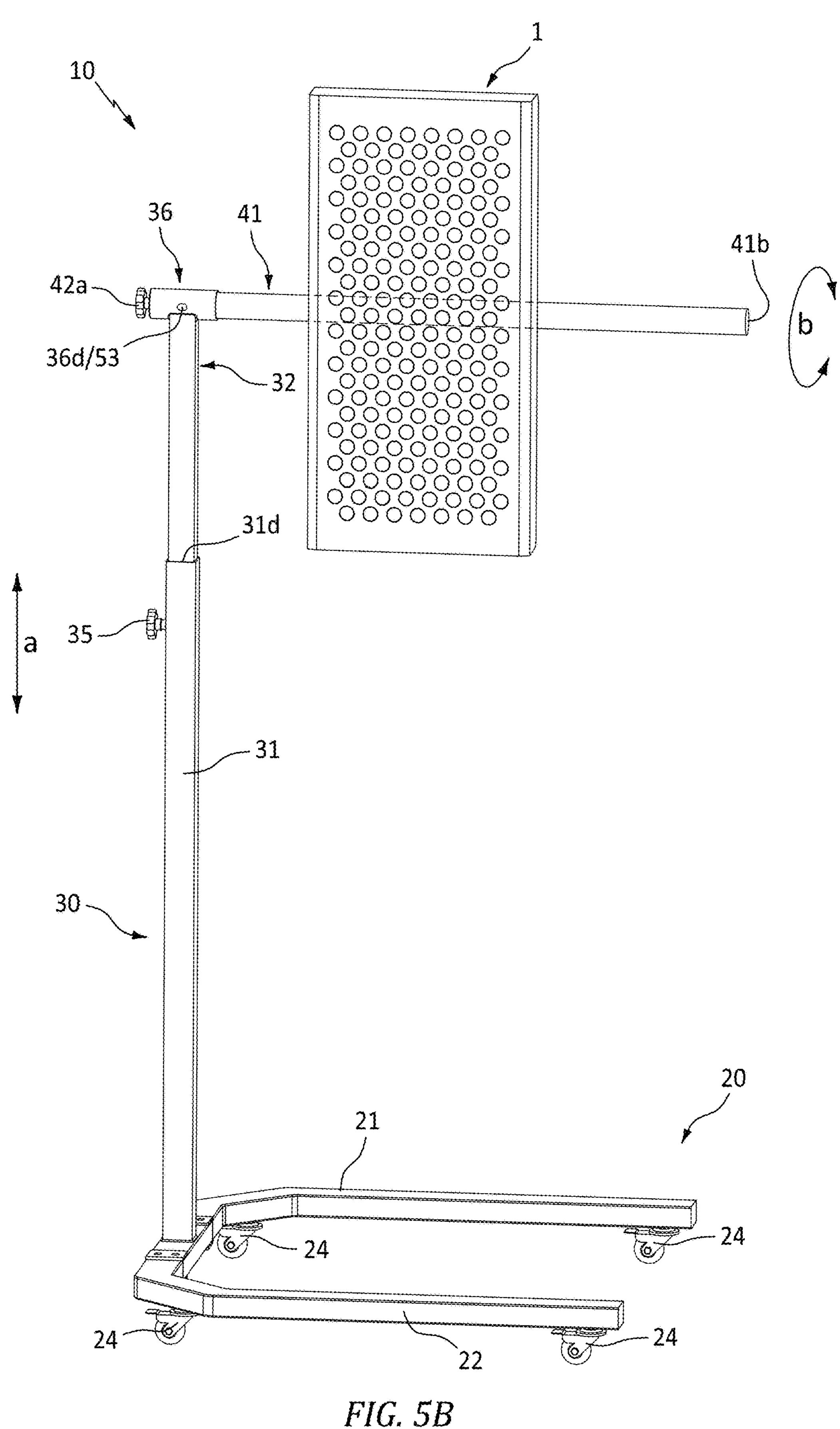
FIG. 5B is a side view of the light therapy device stand in operation, in accordance with one embodiment of the invention.
Figure 5C:
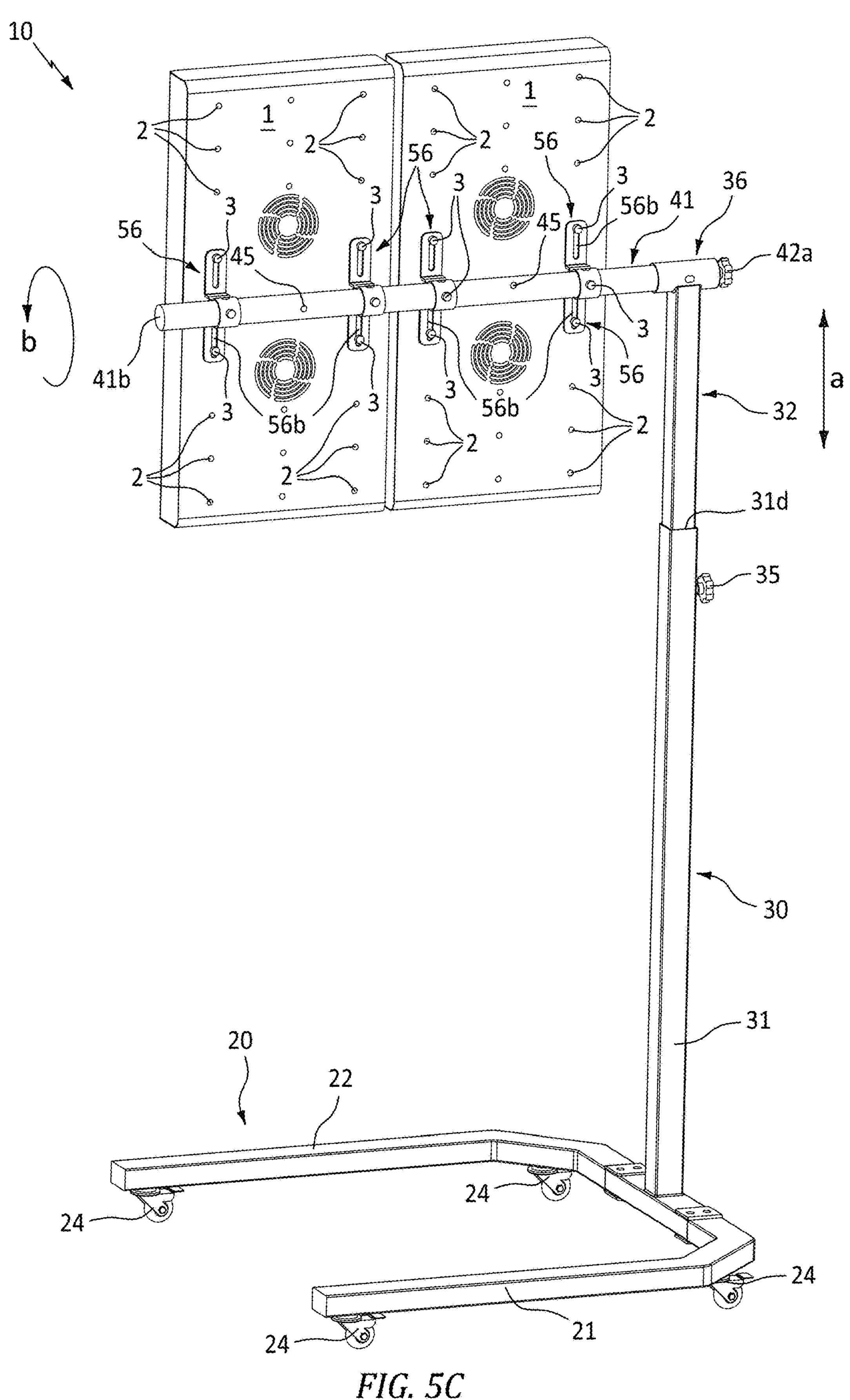
FIG. 5C is another side view of the light therapy device stand in operation, in accordance with one embodiment of the invention.
Figure 5D:
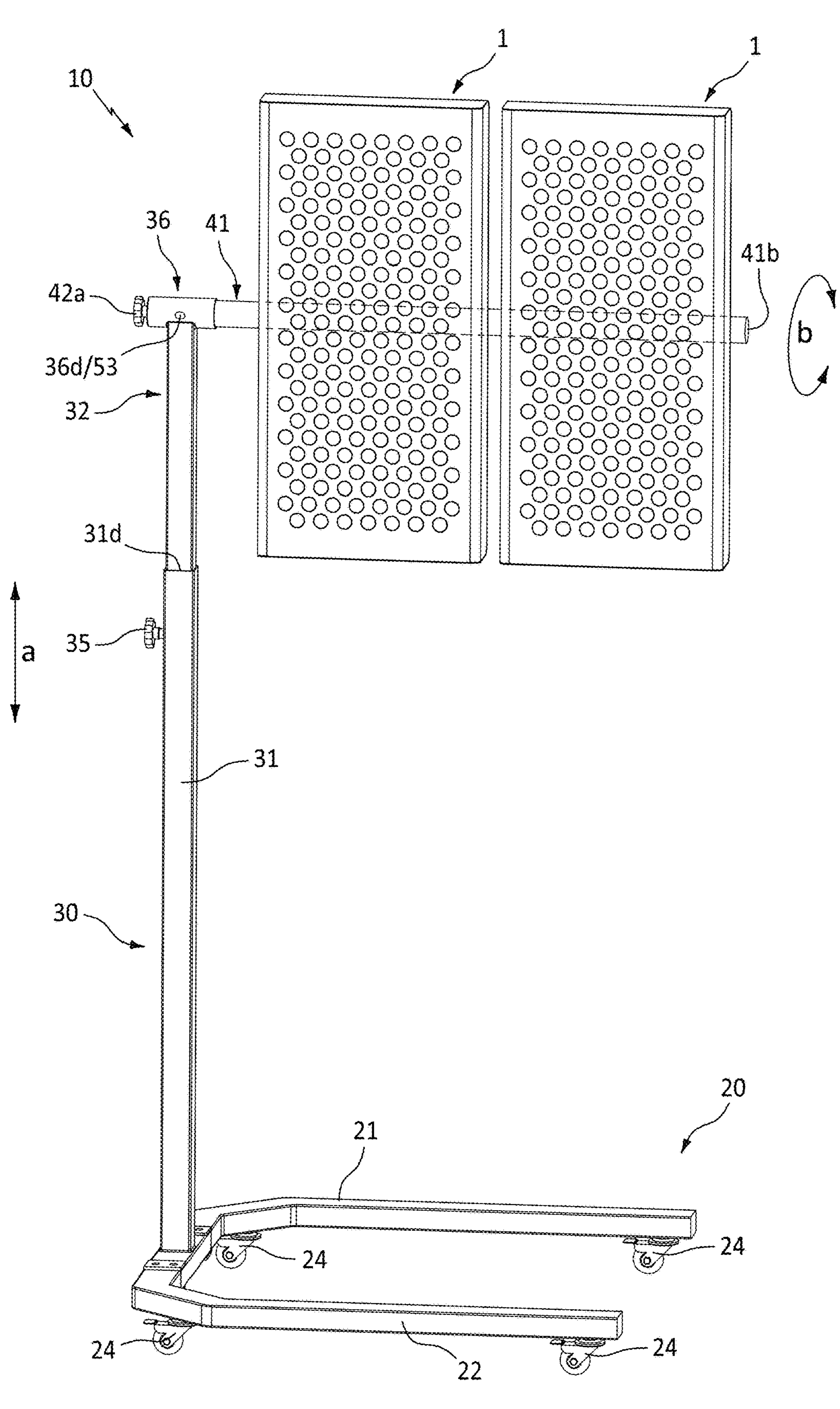
FIG. 5D is another side view of the light therapy device stand in operation, in accordance with one embodiment of the invention.
Figure 5E:
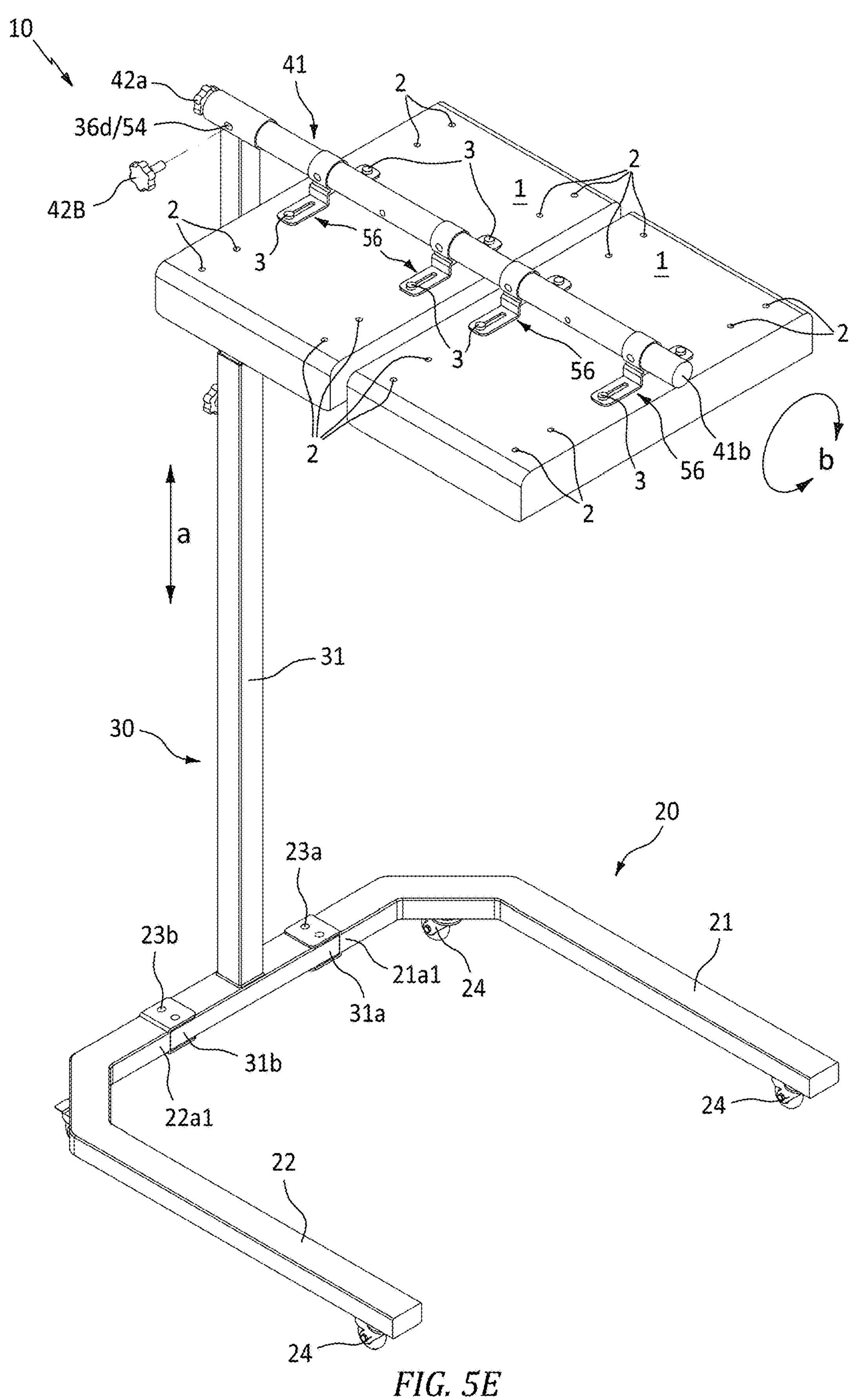
FIG. 5E is a perspective view of the light therapy device stand in operation, in accordance with one embodiment of the invention.
Figure 6A:
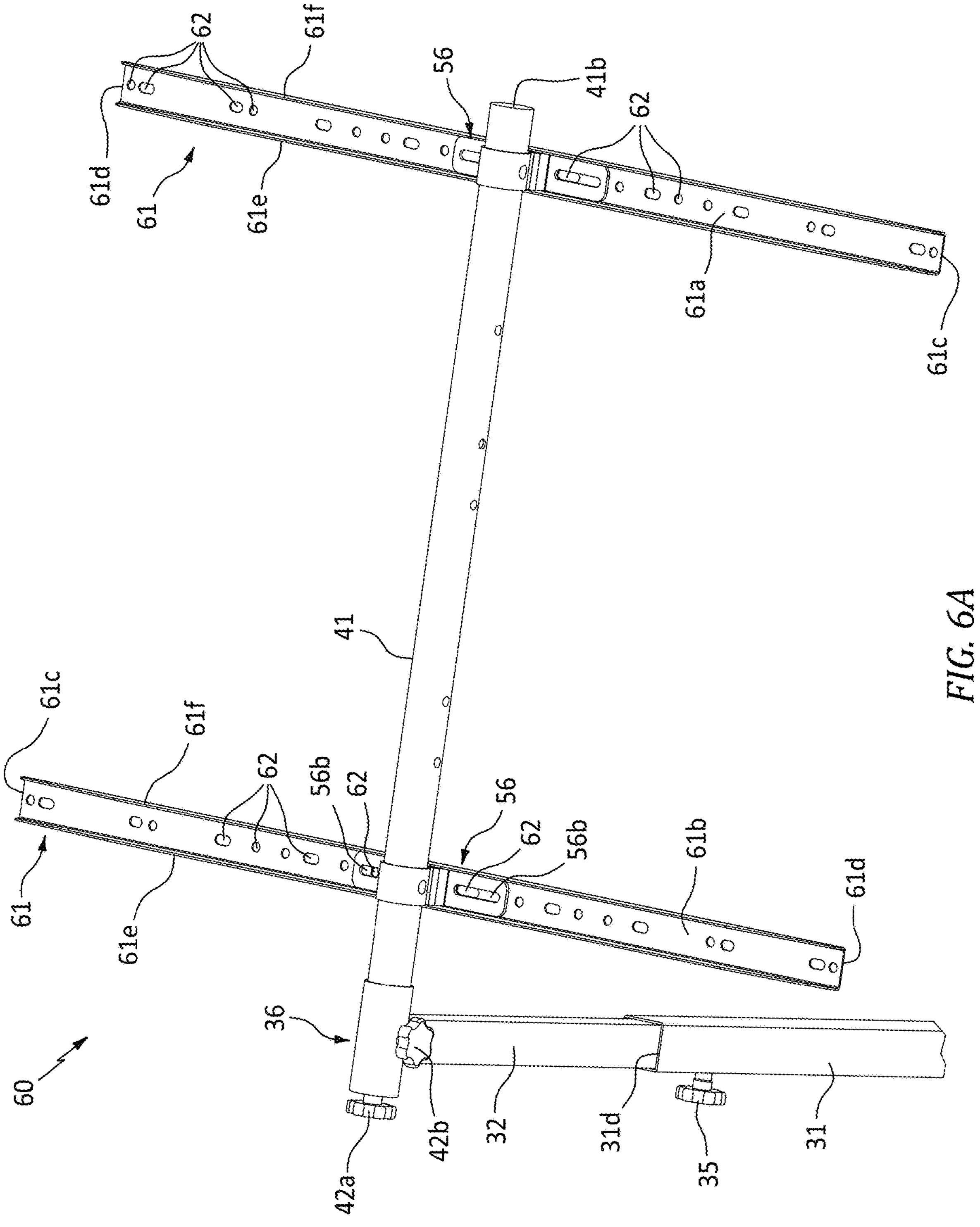
FIG. 6A is a cutout view of the panel attachment assembly of the light therapy device stand, in accordance with one embodiment of the invention.
Figure 6B:
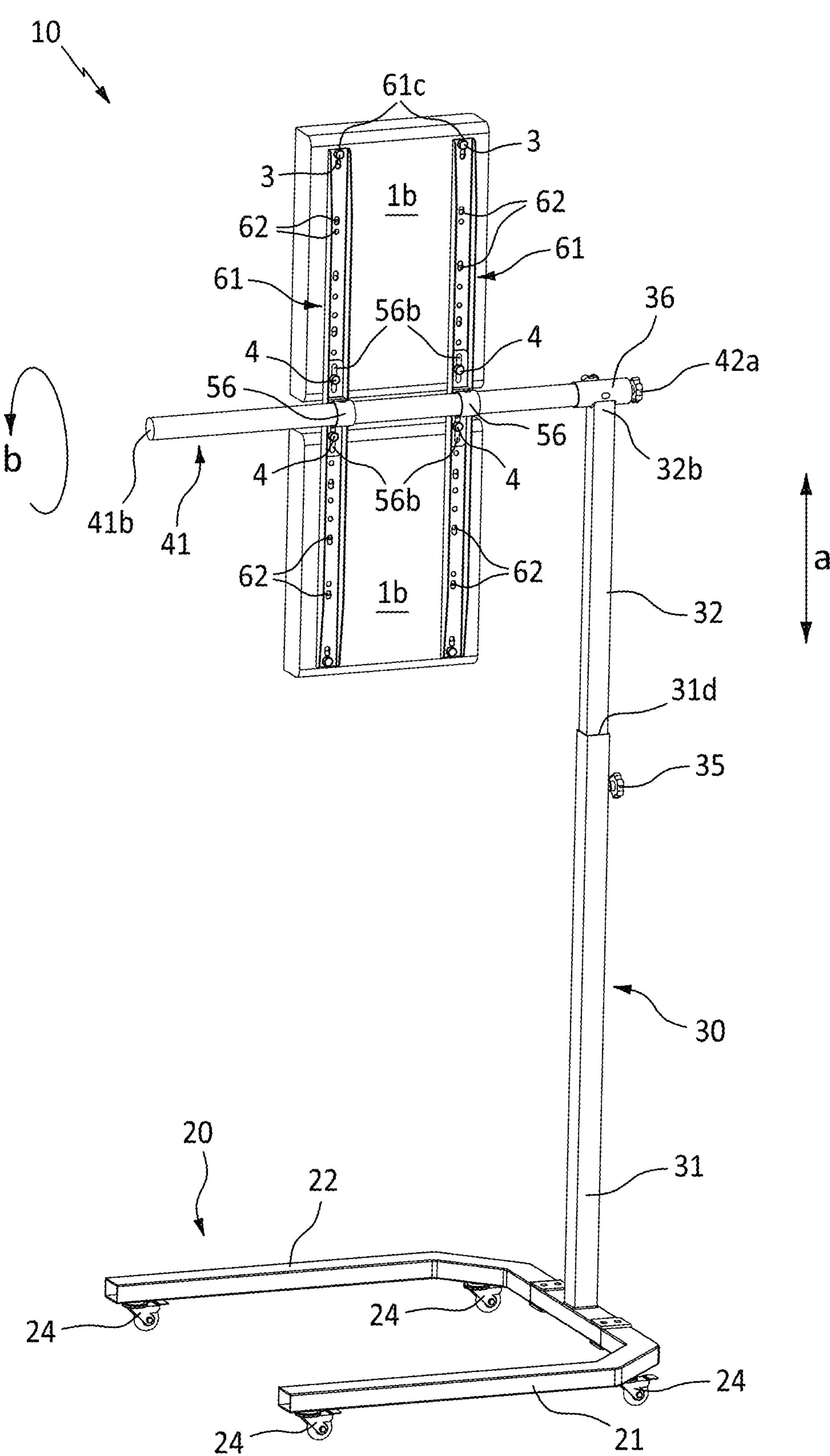
FIG. 6B is a side view of the light therapy device stand in operation, in accordance with one embodiment of the invention.
Figure 6C:
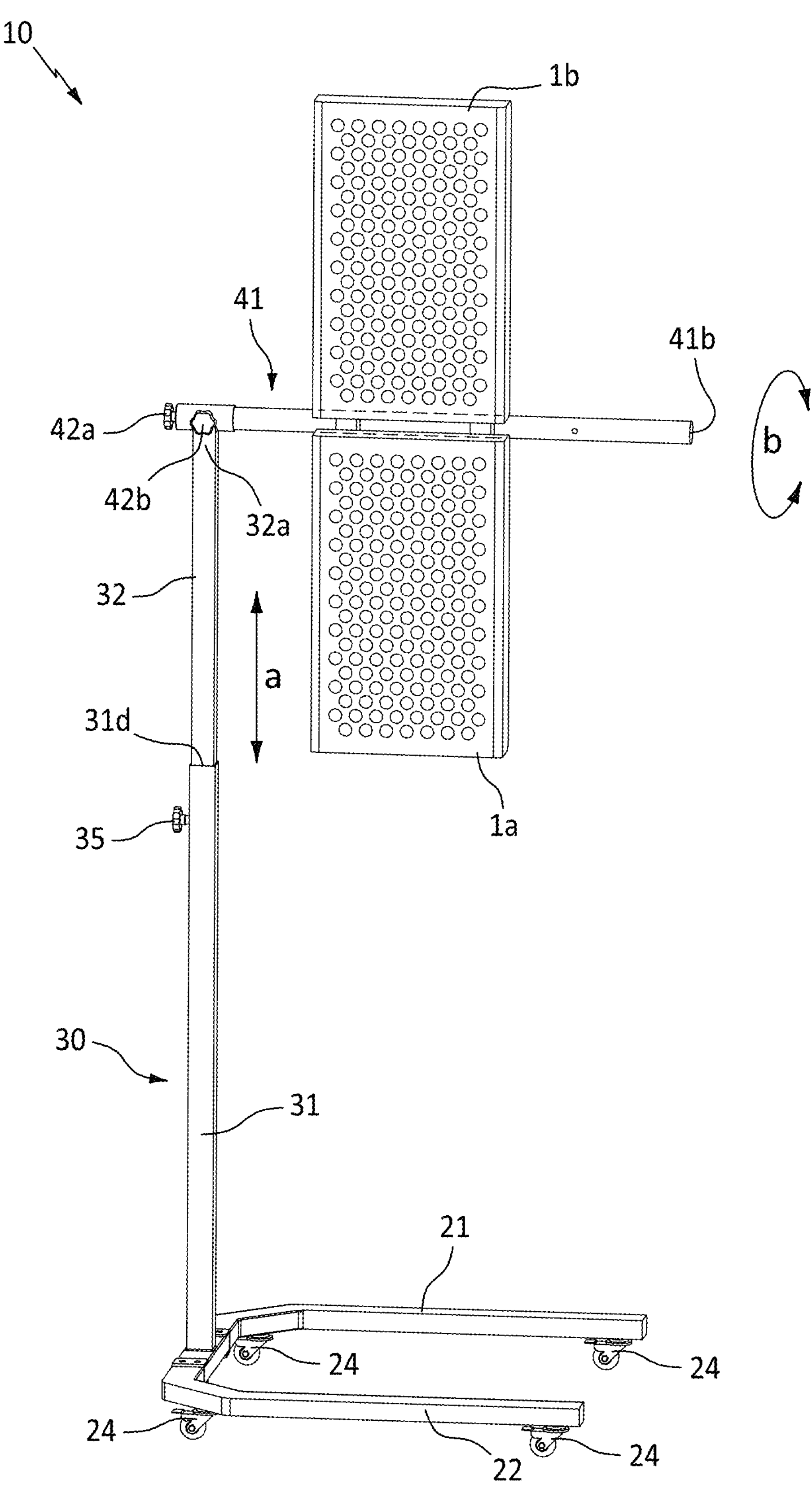
FIG. 6C is another side view of the light therapy device stand in operation, in accordance with one embodiment of the invention.
Figure 6D:
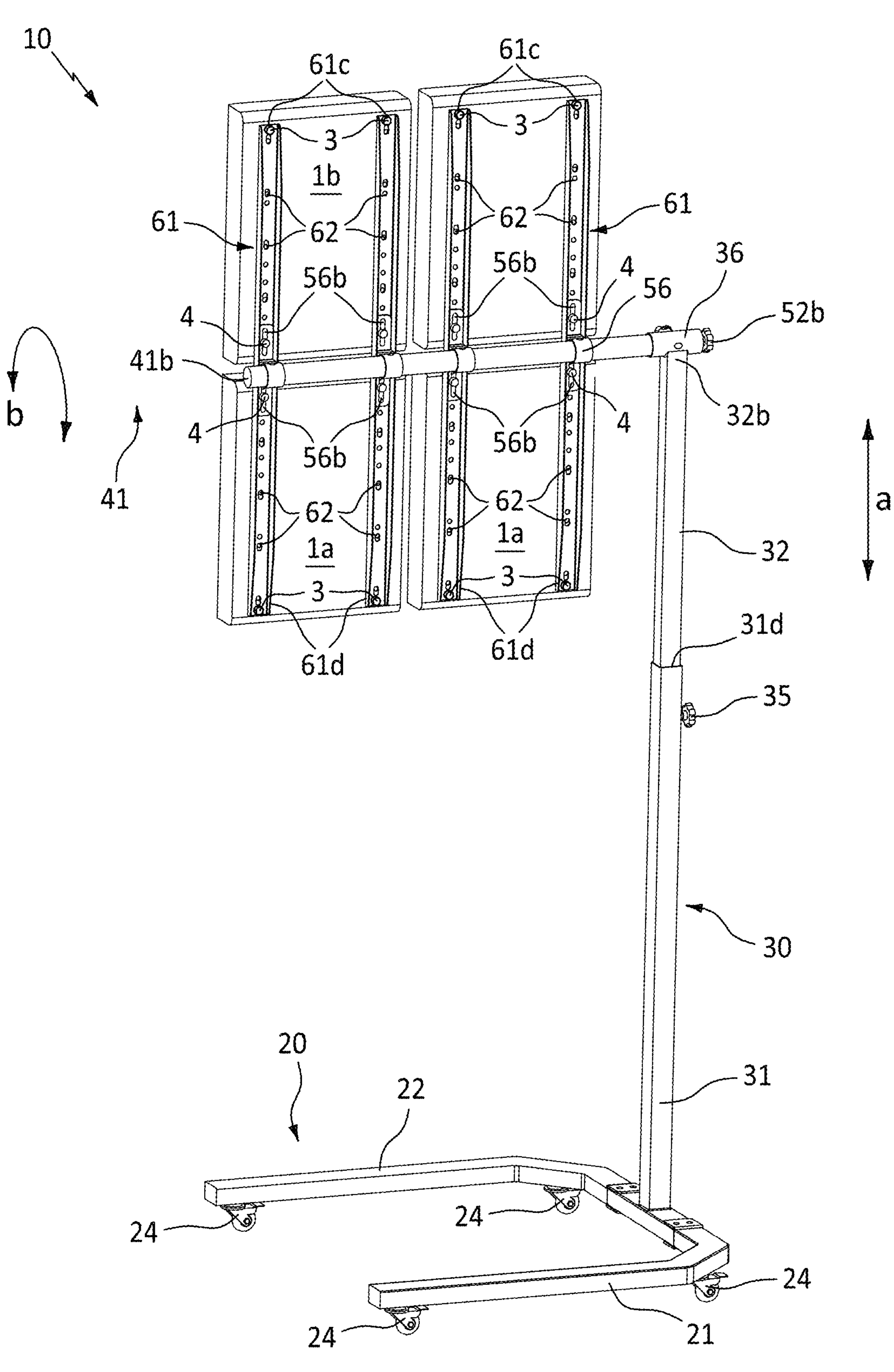
FIG. 6D is another side view of the light therapy device stand in operation, in accordance with one embodiment of the invention.
Figure 6E:
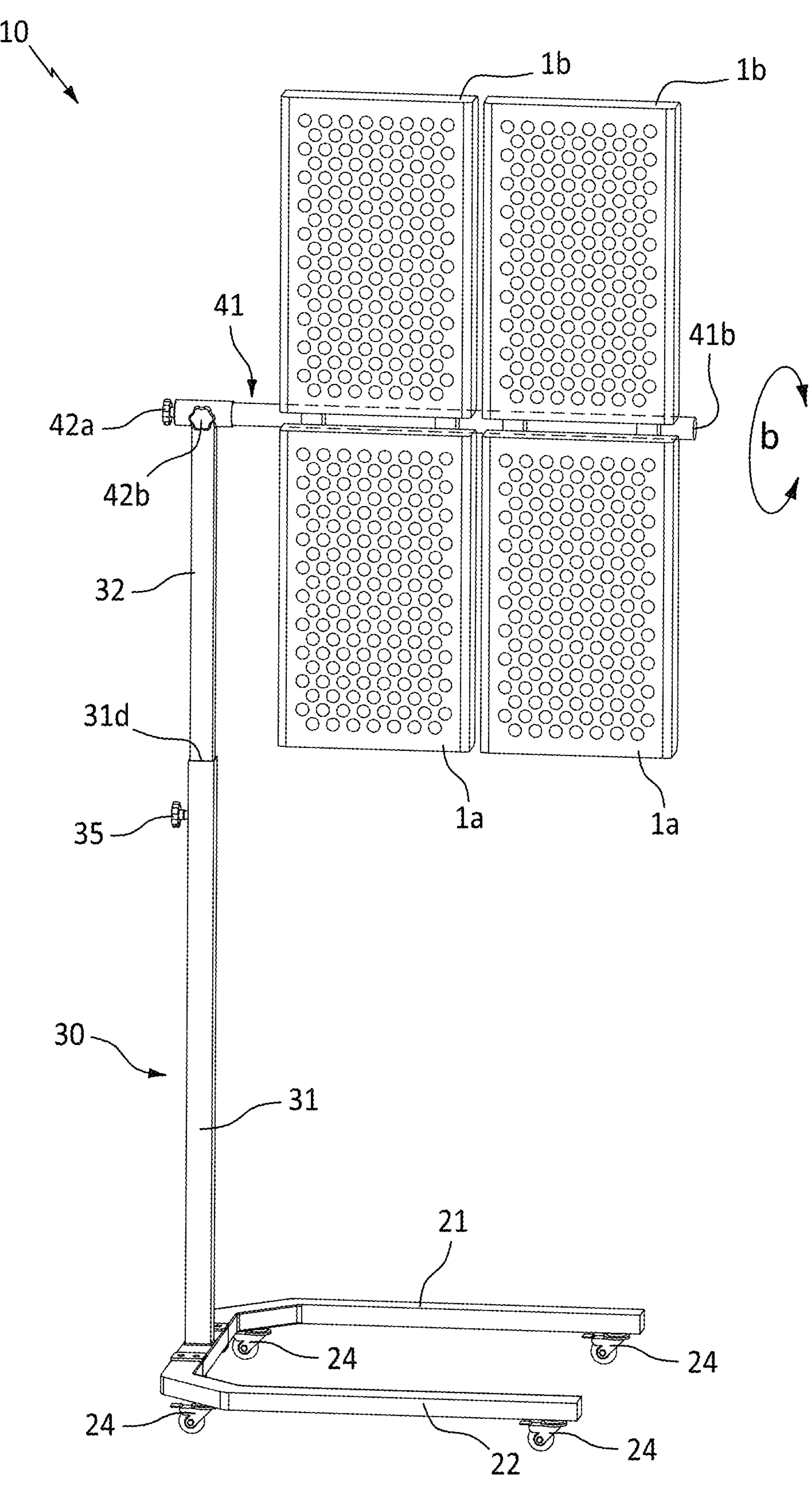
FIG. 6E is another side view of the light therapy device stand in operation, in accordance with one embodiment of the invention.
Figure 6F:
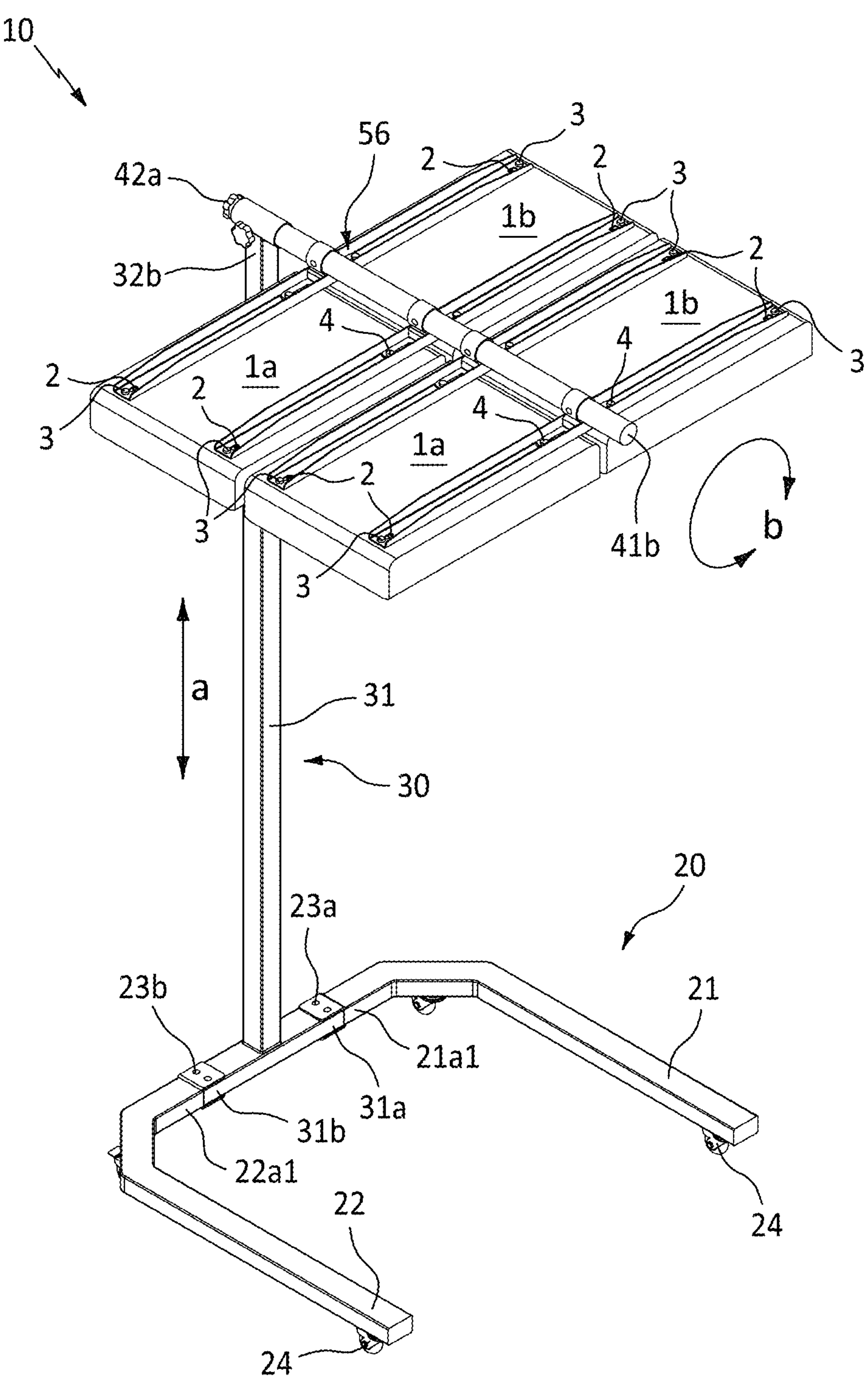
FIG. 6F is a perspective view of the light therapy device stand in operation, in accordance with one embodiment of the invention.
Figure 7A:
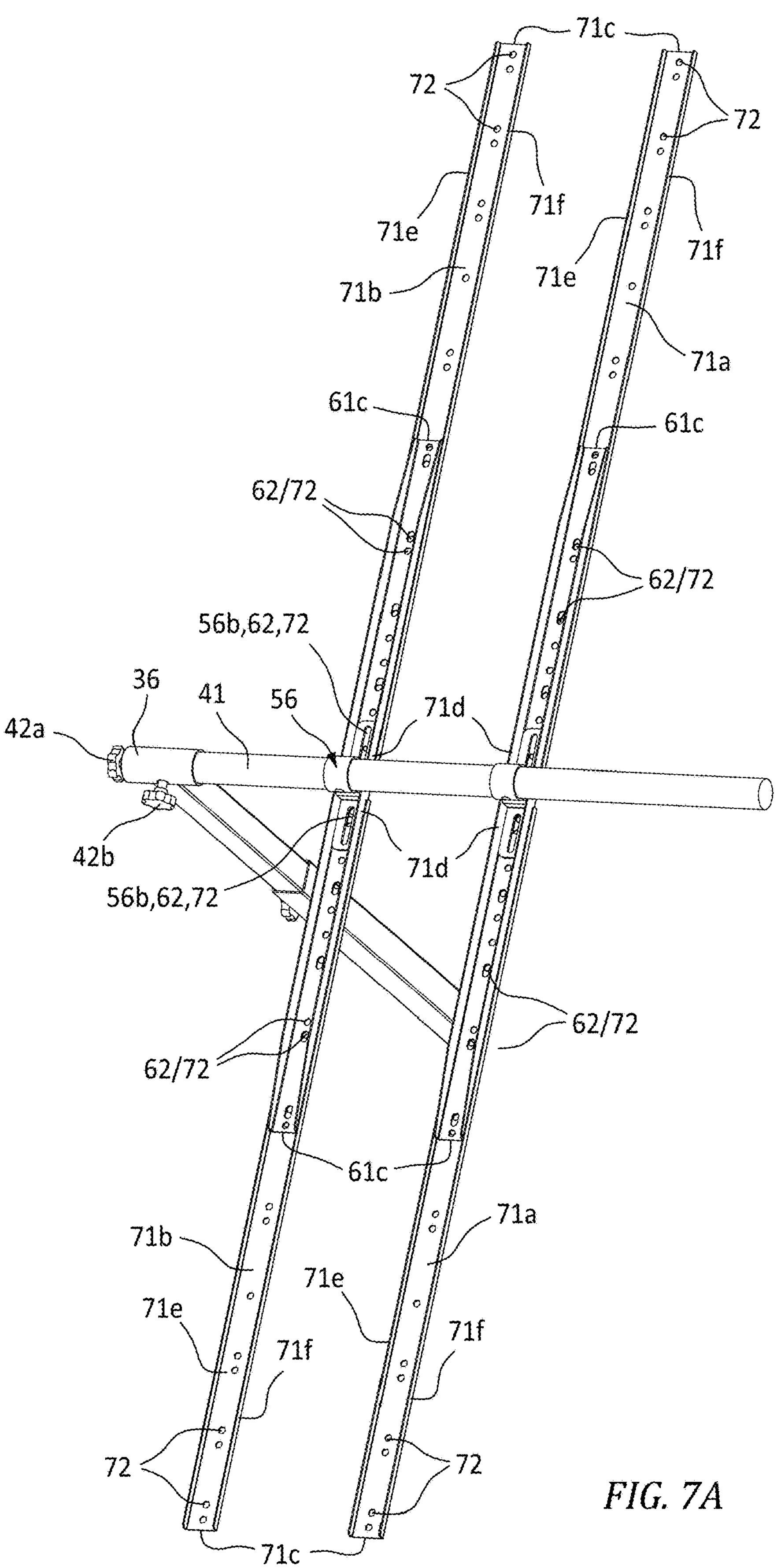
FIG. 7A is another cutout view of the panel attachment assembly of the light therapy device stand, in accordance with one embodiment of the invention.
Figure 7B:
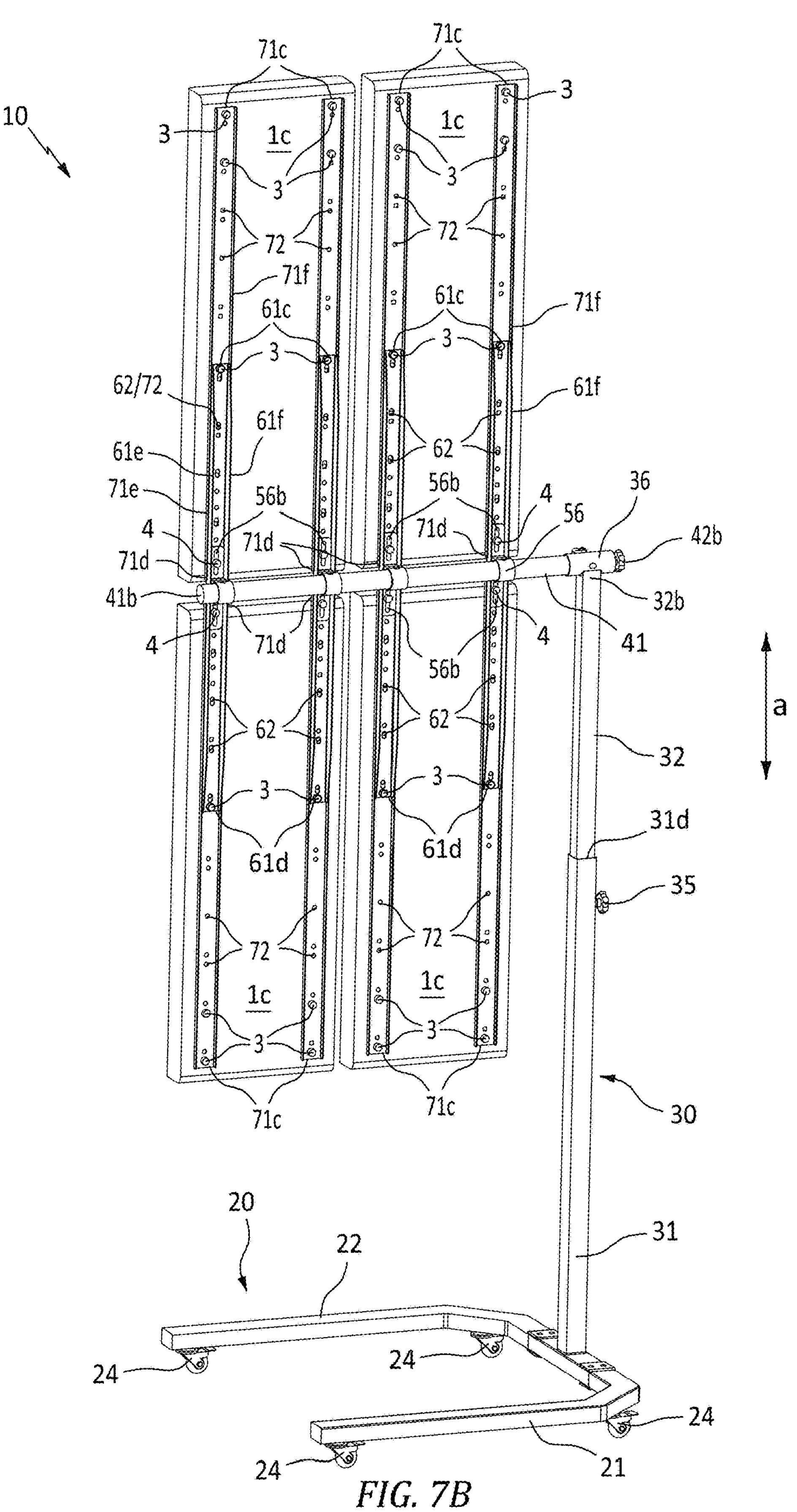
FIG. 7B is yet another side view of the light therapy device stand in operation, in accordance with one embodiment of the invention.
Figure 17C:
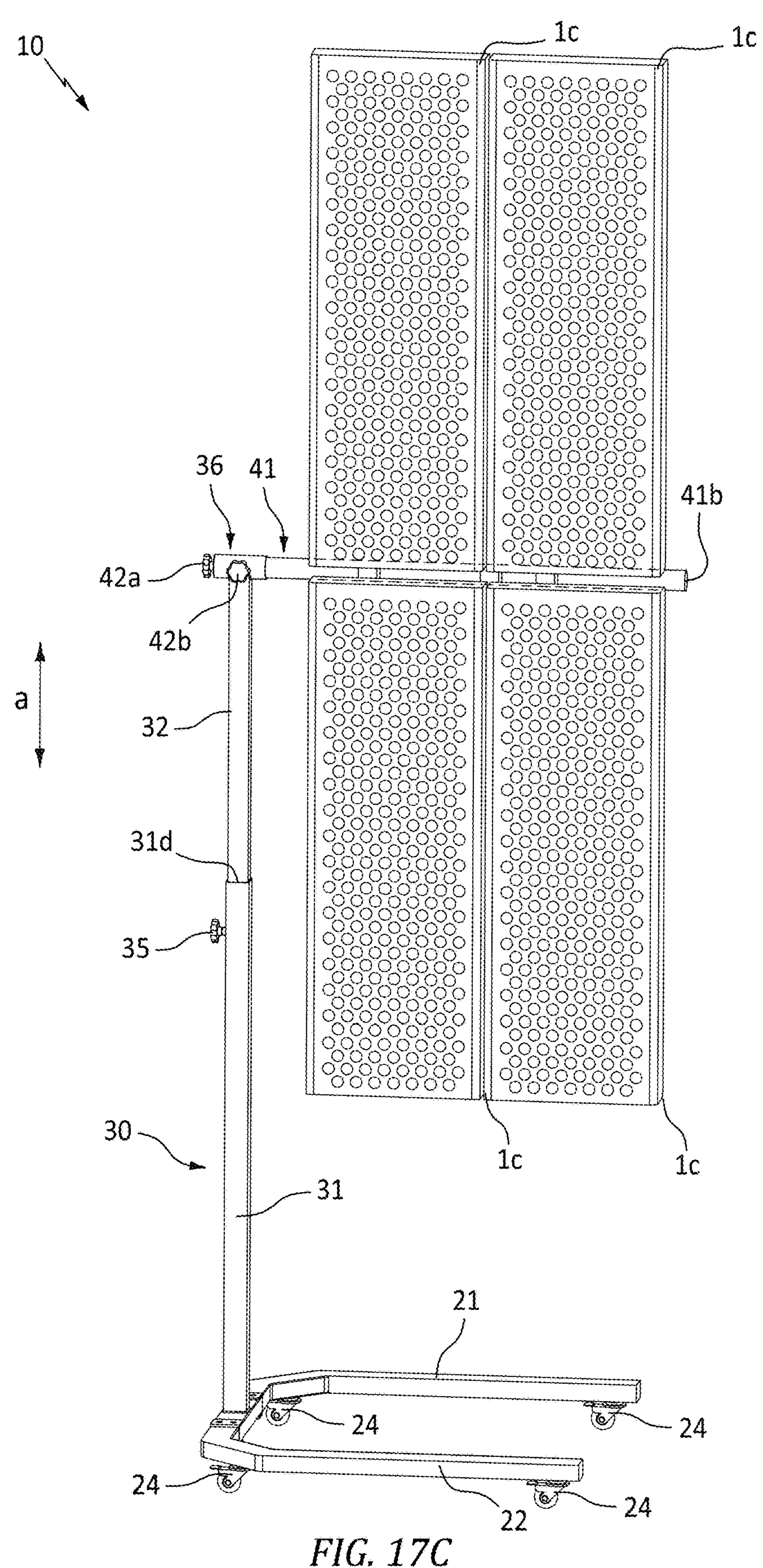
Figure 7D:
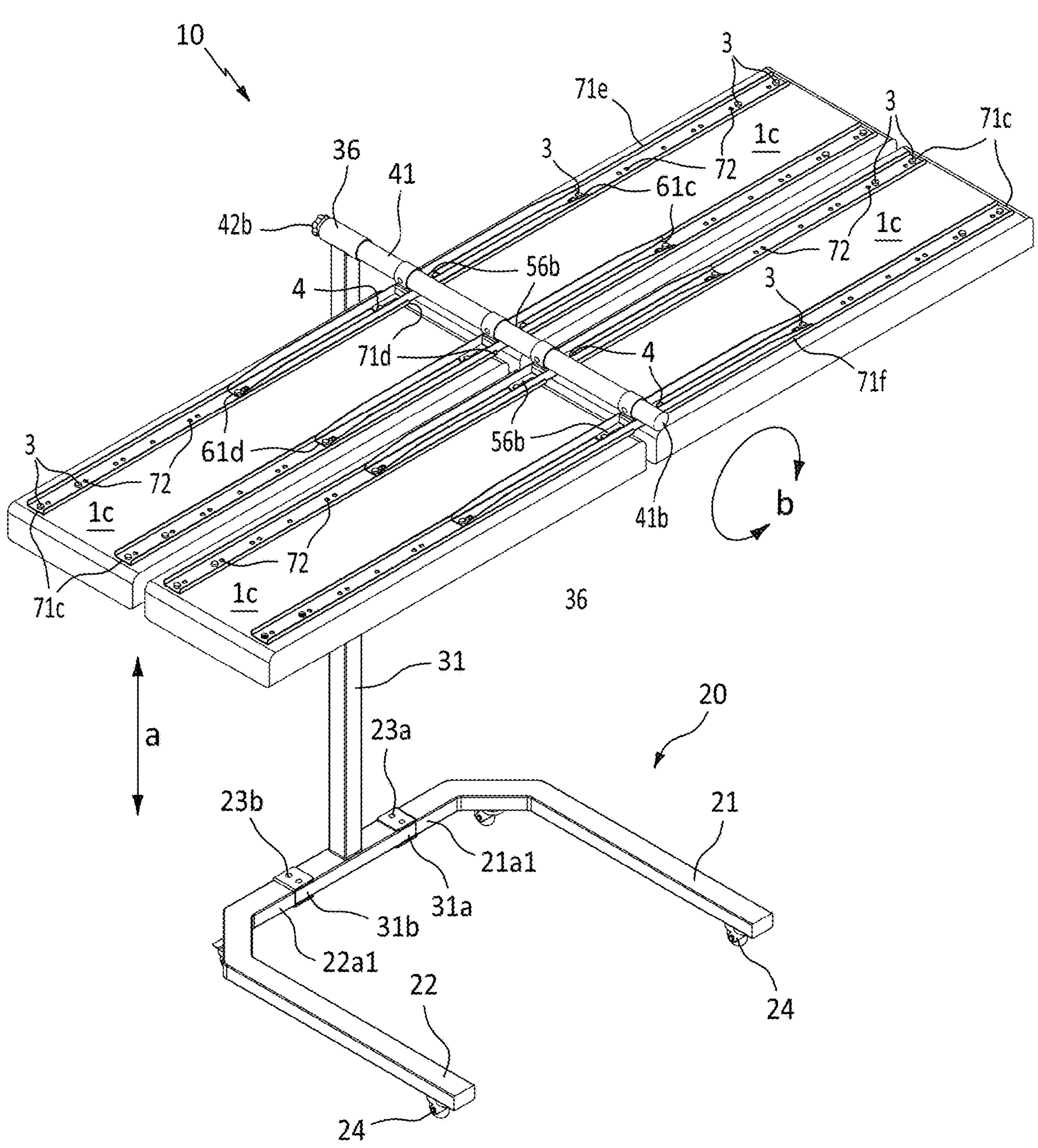
FIG. 7D is yet another perspective view of the light therapy device stand in operation, in accordance with one embodiment of the invention.

As such, when the first end 41*a* of the bar is positioned within the receptacle 36, the bar 41 can rotate (see arrow b) 90° to selectively align either the vertical-positioning threaded opening 43 or the horizontal-positioning threaded opening 44 with the side opening 36*d* of the receptacle 36 to position the light therapy panels in a vertical or horizontal orientation as shown respectively at FIGS. 5E and 5F. Regardless of the orientation, a user can selectively raise and lower the extension arm 30 to position the light therapy device(s) at any number of user-defined heights as shown by arrow a.

As shown at FIGS. 6A-6D, one embodiment of the panel attachment assembly 60 can include a plurality of connection rails 61 that function to engage and secure two standard sized light therapy devices onto the stand in a top to bottom (e.g., stacked) configuration. As shown best at FIG. 6A, each connection rail 61 can include an elongated member having a flat front surface 61*a*, a flat back surface 61*b*, a first end 61*c*, a second end 61*d* and a pair of side rails 61*e* and 61*f* that extend orthogonally outward from the back surface. Each of the rails can also include a plurality of openings 62 that are spaced along the length of the rails so as to be complementary to the locations of the mounting apertures 2 located along the back surface of a light therapy device 1.

In one embodiment, the side rails 61*e* and 61*f* include a separation distance that is complementary to the width of the sliding connector 56, so as to position the arms of the connector against the back surface 61_b_ and between the side rails. When so positioned, the slotted openings 56_b_ will be aligned with at least two of the openings 62 on the rail.

In operation, connector hardware such as elongated bolts 4 can pass through the slotted openings 56_b_ and the respectively aligned opening 62 of the rail to engage mounting apertures 2 located on the top end of one light therapy device 1_a_, and the bottom end of a second light therapy device 1_b_ that are positioned in the stacked configuration. When so positioned, the remaining openings 62 along the rail will be aligned with the other mounting apertures 2 on each light therapy device and can be engaged by mounting hardware 3 such as bolts, for example.

Moreover, when in the stacked configuration, the support bar 41 can be rotated (see arrow b) to position the light therapy devices in either a vertical orientation, or a horizontal orientation, as shown. Regardless of the configuration or orientation, a user can selectively raise and lower the extension arm 30 to position the light therapy device(s) at any number of user-defined heights as shown by arrow a.

In the preferred embodiment, the connection rails will include a length (e.g., distance between first end 61_c_ and second end 61_d_) of about 38 inches. Such a dimension is important to allow the rails to be connected along the full length (from the bottom end to the top end) of two standard sized light therapy devices 1_a_ and 1_b_ such as the BioMax 300 or BioMax 450 light therapy devices that are commercially available from Platinum LED Therapy Lights®, each having a length of about 19 inches. Such a feature prevents the devices from moving relative to each other which could result in uneven alignment with a patient body. Of course, the rails can be manufactured in other dimensions so as to engage two stacked light therapy devices having different dimensions.

FIGS. 7A-7D illustrate one embodiment of the panel attachment assembly 60 that also includes a plurality of extension rails 71 that can used in conjunction with the connection rails 61 to allow the stand 10 to engage and secure two light therapy devices 1_c_ having a stacked dimension of greater than 38 inches.

As shown, each extension rail 71 can include an elongated member having a flat front surface 71_a_, a flat back surface 71_b_, a first end 71_c_, a second end 71_d_ and a pair of side rails 71_e_ and 71_f_ that extend orthogonally outward from the back surface. Each of the extension rails can also include a plurality of openings 72 that are spaced along the length of the rails so as to be complementary to the locations of the connection rail openings 62 and the mounting apertures 2 located along the back surface of a light therapy device 1.

In one embodiment, the side rails 71_e_ and 71_f_ include a separation distance that is complementary to the width of the connection rails 61, so as to position the front surface of a connection rail against the back surface 71_b_ of the extension rail and between the side rails 71_e_ and 71_f_. When so positioned, the sliding connector 56 will engage the connection rail 61 as noted above, and each of the openings 62 and 72 will be aligned with the mounting apertures 2 located along the back surface of a light therapy device 1.

In operation, connector hardware such as elongated bolts 4 can pass through the slotted openings 56_b_ and the respectively aligned openings 62 and 72 of the rails to engage mounting apertures 2 located on the back surface of a light therapy device. When so positioned, the remaining openings 62 and 72 extending the length of the rails will be aligned with the other mounting apertures 2 on the light therapy device and can be engaged by mounting hardware 3 such as bolts, for example.

Moreover, when in the stacked configuration, the support bar 41 can be rotated (see arrow b) to position the light therapy devices in either a vertical orientation, or a horizontal orientation, as shown. Regardless of the configuration or orientation, a user can selectively raise and lower the extension arm 30 to position the light therapy device(s) at any number of user-defined heights as shown by arrow a.

In the preferred embodiment, the extension rails will include a length (e.g., distance between first end 71_c_ and second end 71_d_) of about 36 inches. Such a dimension is important to allow the rails to be connected along the full length (from the bottom end to the top end) of one or more large sized light therapy device 1_c_ such as the BioMax 600 or BioMax 950 light therapy devices commercially available from Platinum LED Therapy Lights®, each having a length of 36 inches. Of course, the rails can be manufactured in other dimensions so as to engage light therapy devices having different dimensions.

Accordingly, the inventive stand 10 can allow a user to securely position any number of individual light therapy devices individually, in a side-by-side configuration and/or in a stacked configuration, and to orient the same anywhere between a purely horizontal and purely vertical position. Such a feature permits the inventive stand 10 to position one or more light therapy devices for use by a user when standing (with the devices positioned vertically) or when laying on a treatment table (with the light therapy devices positioned horizontally). Moreover, such a feature allows users to easily move the entire system from one location to another without removing, disconnecting, or adjusting the position of the light therapy devices individually.

As to a further description of the manner and use of the present invention, the same should be apparent from the above description. Accordingly, no further discussion relating to the manner of usage and operation will be provided.

As described herein, one or more elements of the light therapy device stand 10 can be secured together utilizing any number of known attachment means such as, for example, screws, glue, compression fittings and welds, among others. Moreover, although the above embodiments have been described as including separate individual elements, the inventive concepts disclosed herein are not so limiting. To this end, one of skill in the art will recognize that one or more individually identified elements may be formed together as one or more continuous elements, either through manufacturing processes, such as welding, casting, or molding, or through the use of a singular piece of material milled or machined with the aforementioned components forming identifiable sections thereof.

The terminology used herein is for the purpose of describing particular embodiments only and is not intended to be limiting of the invention. As used herein, the singular forms "a," "an," and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. Likewise, the term "consisting" shall be used to describe only those components identified. In each instance where a device comprises certain elements, it will inherently consist of each of those identified elements as well.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated.

What is claimed is:

1. A light therapy device stand, said stand comprising:

a base that includes a first base member having a first end, a second end, and a curved section, and a second base member having a first end, a second end, and a curved section;

an extension arm that includes a fixed arm section having a first end that is connected to the first end of the first base member, a second end that is connected to the first end of the second base member, and a third end that extends orthogonally from the first and second base members, said fixed arm section including a hollow interior space and an opening along the third end; and a sliding arm section having a bottom end that is positioned within the hollow interior space of the fixed arm section;

a receptacle that is positioned along a top end of the sliding arm section;

an elongated support bar that is configured to be connected to the receptacle;

at least one connector that is configured to engage each of the elongated support bar and a back surface of a light therapy device;

a plurality of sliding connectors that are slidingly engaged with the support bar, each of the plurality of sliding connectors including a cylindrical shaped center section and two serially aligned connection arms;

a plurality of threaded openings that are positioned along the support bar;

a central opening that is located along the cylindrical shaped center section; and a pair of slotted openings located along the two serially aligned connection arms.

2. The stand of claim 1, wherein the sliding arm section is telescopically connected to the fixed arm section.

3. The stand of claim 2, wherein the extension arm is configured to transition between an extended position and a retracted position.

4. The stand of claim 3, wherein in the extended position the light therapy device is moved away from the base, and in the retracted position the light therapy device is moved toward the base.

5. The stand of claim 1, wherein the receptacle includes an open first end, and the elongated support bar includes a first end that is removably positioned within the open first end of the receptacle.

6. The stand of claim 5, wherein the receptacle includes an opening along a second end, and the first end of the support bar includes a threaded aperture.

7. The stand of claim 6, wherein the support bar is secured to the receptacle via hardware that extends through the opening and engages the threaded aperture.

8. The stand of claim 1, wherein each of the plurality of sliding connectors are secured onto the support bar via hardware that extends through the central opening and engages one of the plurality of threaded openings.

9. The stand of claim 1, wherein each of the pair of slotted openings includes a shape and location that is complementary to a shape and a location of a mounting aperture located on the light therapy device.

10. The stand of claim 1, wherein the light therapy device is secured onto the plurality of sliding connectors via hardware that extends through the slotted openings and engages a complementary mounting aperture.

* * * * *